United States Patent [19]

Norquest et al.

[11] Patent Number: 4,881,644

[45] Date of Patent: Nov. 21, 1989

[54] TAMPON APPLICATOR WRAP

[75] Inventors: Robert C. Norquest, Dover; Kevin M. Coverdale, Hartley, both of Del.

[73] Assignee: Playtex Family Products Corporation, Stamford, Conn.

[21] Appl. No.: 245,832

[22] Filed: Sep. 16, 1988

[51] Int. Cl.⁴ ............................................. B65D 83/10
[52] U.S. Cl. .................................. 206/363; 206/627; 604/16
[58] Field of Search ................. 604/15–18; 206/438, 363, 440, 627

[56] References Cited

U.S. PATENT DOCUMENTS

| | | |
|---|---|---|
| 1,848,119 | 3/1932 | Fairchild . |
| 1,864,968 | 6/1932 | Weiner . |
| 1,965,353 | 7/1934 | Nones . |
| 2,057,121 | 10/1936 | Trevellyan . |
| 2,195,740 | 4/1940 | Salfisberg . |
| 3,092,251 | 6/1963 | Jaggers ................................. 206/438 |
| 3,179,327 | 4/1965 | Burton et al. . |
| 3,186,628 | 6/1965 | Rohde . |
| 3,197,120 | 7/1965 | Sparks . |
| 3,216,562 | 11/1965 | Lockwood . |
| 3,625,351 | 12/1971 | Eisenberg . |
| 4,617,781 | 10/1986 | Ingersoll et al. . |
| 4,620,534 | 11/1986 | Zartman ................................. 604/15 |
| 4,648,513 | 3/1987 | Newman . |

*Primary Examiner*—Carroll B. Dority
*Attorney, Agent, or Firm*—Stewart J. Fried

[57] ABSTRACT

There is provided a wrap for a tampon applicator having a first member and a second member. The wrap includes a hollow body for containing the tampon applicator therein, and a score line located at a predetermined position on the body to separate the body into two discrete portions in the vicinity of the junction of the first and the second members of the tampon applicator.

8 Claims, 1 Drawing Sheet

4,881,644

TAMPON APPLICATOR WRAP

BACKGROUND OF THE INVENTION

1. Field of the Invention

The present invention relates generally to tampon wrap and, more particularly, to a tampon applicator wrap having an easy open, detachable top.

With today's active woman and the need to change tampons frequently during the menstrual period, it is desired to provide tampons having applicators that are readily and conveniently carried on ones person. Therefore, it is necessary to provide a wrap that protects the tampon and tampon ejection end of the applicator from being soiled. Accordingly, the wrap must be made of a material that is strong enough so as not to inadvertently open. However, it is also necessary that the user have the ability to open the wrap when desired without, of course, soiling the tampon ejection end of the applicator.

It is desired that such a wrap also provide for the disposal of the used tampon applicator. It is also desired that such a wrap be inexpensively produced and, therefore, that it be made from readily available materials. For a two piece compact tampon applicator, it is highly desirable that the wrap permit the user to assemble the applicator without touching the tampon ejection end of the applicator.

2. Description of the Prior Art

The use of material for a tampon wrap which is strong enough to prevent inadvertent opening is known. For example, the tampons presently marketed by the assignee of the present application under the registered trademark Playtex (of Playtex Apparal, Inc.) use a polypropylene wrap. The end seals of this wrap are described in U.S. Pat. No. 4,617,781 to Ingersoll, et al, which issued on Oct. 21, 1986, and is also owned by the assignee of the present application. The polypropylene wrap is specifically a voided polypropylene film wrap. In order to open the wrap, there is provided a row of notches at the each end seal of the wrap as described in the Ingersoll, et al patent. Further, the wrap is virtually always destroyed when opened thereby making it unavailable for disposing of the used tampon applicator.

The use of a weakening line or a scoring or the like to open a package is known. For example, U.S. Pat. No. 3,625,351 to Eisenberg, which issued on Dec. 7, 1971, is directed to a sterilized tearable bag made of polyvinyl chloride having a pair of aligned striations comprising a multitude of closely spaced grooves or indentations which facilitate tearing of the bag. Also, U.S. Pat. No. 3,186,628 to Rohde, which issued on June 1, 1965, is directed to a package for a syringe formed from various materials, including polypropylene, which package has opposed coinciding score groove lines which rupture by grasping the package at its opposed ends.

Further, U.S. Pat. No. 1,848,119 to Fairchild, which issued on Mar. 8, 1932, is directed to a wrapper for toilet paper which has a weakened line formed by scoring; U.S. Pat. No. 1,864,968 to Weiner, which issued on June 28, 1932, is directed to a carton having a circumferential line formed by scoring or perforations to enable the carton to separate; and U.S. Pat. No. 1,965,353 to Nones, which issued on July 3, 1934, is directed to a wrapper for a bottle which has a weakening line formed by scoring. Still further examples of the use of a weakening line or a scoring or the like to open a package are U.S. Pat. No. 3,197,120 to Sparks, which issued on July 27, 1965, for a clamshell envelope; U.S. Pat. No. 3,216,562 to Lockwood, which issued on Nov. 9, 1965, for an easy-open capsule; U.S. Pat. No. 3,179,327 to Burton, et al., which issued on Apr. 20, 1965, for a film tear line for plastic film material; U.S. Pat. No. 2,195,740 to Salfisberg, which issued on Apr. 2, 1940, for separating bags from a row of formed bags; and U.S. Pat. No. 2,057,121 to Trevellyan, which issued on Oct. 13, 1936, for packaging for fibrous material.

Heretofore, while there have been tampon wraps such as the Playtex Family Products, Inc. wrap, mentioned above, which is the subject of U.S. Pat. No. 4,617,781 to Ingersoll, et al, also mentioned above, there has not been a tampon wrap which achieves all of the desired objectives set forth above. For example, U.S. Pat. No. 4,648,513 to Newman, which issued on Mar. 10, 1987, is directed to a package for sanitary napkins, and also a tampon, which package can also turn into a disposal container or wrap for the used sanitary napkin or tampon. Specifically, the package or container, which is made from a sheet of material such as polypropylene or polyethylene, has a pair of perforation lines that form tear lines basically at both ends of the wrap past the enclosed tampon. There is also included a flap which is used to reseal the package after the used article is placed therein. Significantly, this package, which is used for regular sized or non-compact applicators, does not address the problem of providing for selected grasping of the applicator without touching or otherwise soiling the tampon ejection end of the applicator. Also, because of the addition of the flap, this package is relatively more expensive. Further, because the tear lines are beyond the enclosed product a great deal of wrap material is wasted making this wrap even more costly and, moreover, the overall length of the applicator with package is increased.

SUMMARY OF THE INVENTION

It is an object of the present invention to provide a tampon applicator wrap which easily opens at a predetermined location.

It is another object of the present invention to provide such a tampon applicator wrap which can be used for any type of tampon applicator.

It is still another object of the present invention to provide such a tampon applicator wrap which is strong enough so as not to inadvertently open.

It is yet another object of the present invention to provide such a tampon applicator wrap which is easily opened by the user when desired.

It is still yet another object of the present invention to provide such a tampon applicator wrap which opens to form two discrete portions with at least one portion retaining its integrity so that it can also be used to dispose of the tampon applicator after use.

It is yet still another object of the present invention to provide such a tampon applicator wrap which opens at a predeterimed location thereby virtually assuring that the user shall not touch or otherwise soil the tampon ejection end of the applicator.

To the accomplishments of the foregoing objects and advantages, the present invention, in brief summary, comprises a wrap for a tampon applicator having a first or barrel member and a second or plunger member. The wrap comprises a hollow body for containing the tampon applicator therein, and a score line located in a predetermined position on the body to separate the body into two discrete portions, preferably, in the vicinity of the junction of the first and second members of the tampon applicator.

BRIEF DESCRIPTION OF THE DRAWINGS

The foregoing and still other objects and advantages of the present invention will be more apparent from the following detailed explanation of the preferred embodiments of the invention in connection with the accompanying drawings wherein.

DESCRIPTION OF THE PREFERRED EMBODIMENTS

Figure 1:
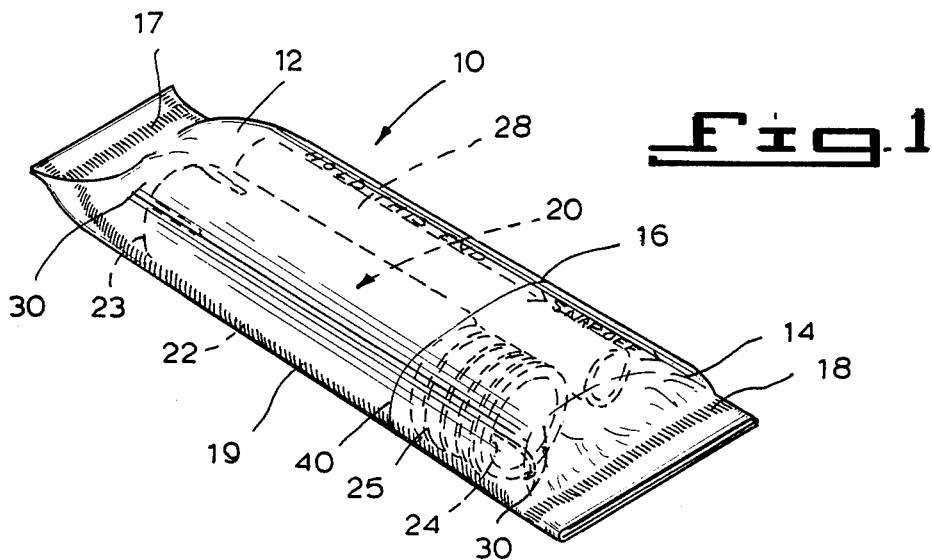
FIG. 1 is a perspective view of the wrap of the present invention.

Referring to the drawings and, in particular, FIG. 1, there is provided a tampon applicator wrap generally represented by reference numeral 10. The wrap 10 is adapted to enclose therein a tampon applicator 20. The tampon applicator 20 shown in the figures of the present application includes a discrete barrel 22, which is adapted to contain a tampon therein, and a discrete plunger 28. The shown tampon applicator 20, which is the subject of a co-pending application Ser. No. 245,888, filed on even date, is representative of one of the preferred types of tampon applicators that can be contained within the tampon wrap 10 of the present application. However, it is understood that the tampon wrap 10 can be used for any sized and any type of tampon applicator, and can possibly even be used for a digital tampon.

The wrap 10 includes a body which, when desired, separates into a main portion 12 and a top portion 14. The wrap 10 is formed from a flat sheet of polyproylene material. Polypropylene material is preferred since it is strong enough so as not to tear easily or inadvertently, and is resistant to transmission of water and odors. Further, polypropylene is heat sealable thereby making it easy to work with from a production standpoint and is relatively inexpensive. However, other materials which resist inadvertent tearing, such as polyethylene, may also be used.

A particularly preferred polypropylene is voided film polypropylene which has air bubbles within the polypropylene film itself. By creating these air bubbles, the voided polypropylene is less dense than pure polypropylene which facilitates sealing of the wrap, yet retains all the desired properties discussed above. Such voided polypropylene is being sold under the trademark of Hercules R WT503 (Hercules is a registered trademark of Hercules Incorporated). Since polypropylene is a relatively strong or tear resistant material, it is generally understood that means should be provided to open the polypropylene wrap. Heretofore, a row of notches in the end seal have been provided to open a polypropylene wrap as described in U.S. Pat. No. 4,617,781, discussed above, which is incorporated herein by reference.

In its initial or unopened state, shown in FIG. 1, the main portion 12 and the top portion 14 of the wrap 10 meet at a single line 16. Line 16 is a crush or score line that serves as a weakening area for subsequent separation of the main portion 12 from the top portion 14 to thus open the wrap. It is important that the score line 16 be a failure or crush line about the wrap which does not inadvertently open as one carries the wrapped tampon applicator. Specifically, the wrap 10, as shown in FIG. 1, includes a pair of end seals 17, 18 and a longitudinal or axial seal 19 which seals can be made in accordance with the teachings of U.S. Pat. No. 4,617,781 to Ingersoll, et al., discussed above. The pair of end seals 17, 18 are formed circumferentially on the wrap 10 in a plane basically perpendicular to the axial direction of the wrap 10. The score line 16 is also formed circumferentially on the wrap 10. The score line 16 is, preferably, formed in a plane which is basically parallel to the planes of the end seals 17, 18. Accordingly, a single score line is preferred because if two or more score line were provided, the wrap, especially between the score lines, may break into fragments when a user opens the wrap.

Figure 2:
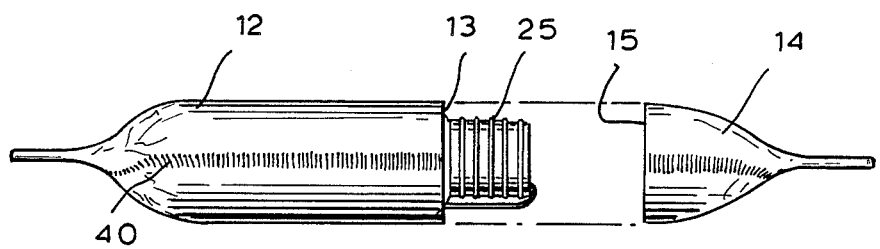
FIG. 2 is a side view of the wrap of FIG. 1 with the top of the wrap separated from the body of the wrap.

FIG. 2 illustrates the wrap 10 after the top portion 14 has been separated from the main portion 12. The edge 13 of the main portion and the edge 15 of the top portion, which edges define the score line prior to separation, should be even, i.e. without the jaggedness which would otherwise accompany the tearing of a polypropylene wrap after separation. This construction assures that the wrap 10 will separate cleanly, i.e. in a straight line, into the main portion 12 and the top portion 14 so that the integrity of at least the main portion 12 is retained. Thus, the main portion 12, which remains substantially intact, can be used to store or otherwise dispose of the used tampon applicator 20.

The score line 16 is formed when the film is in its flat state by passing the film between a pair of rollers with one roller being fitted with a blade and the other a flat portion or anvil. The score line is formed at ambient temperature. It has been found that score line 16 so formed requires a force of approximately 4 to 9 lbs. of pressure to be pulled apart.

Figure 3:
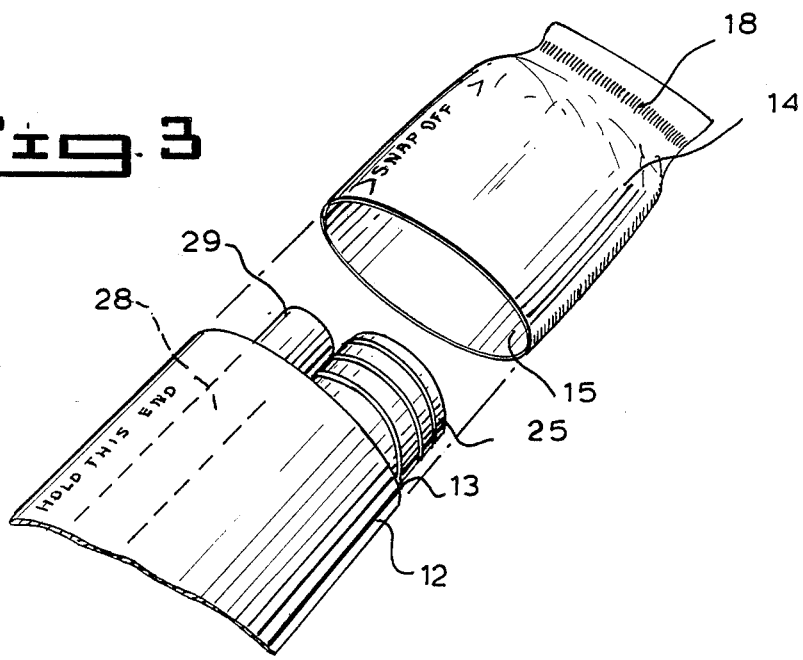
FIG. 3 is a partial perspective view of the wrap of FIG. 1 turned ninety degrees with the top of the wrap separated from the body of the wrap.

A preferred tampon applicator 20 for use in connection with the subject wrap 10 is illustrated in the FIGS. 1–3. However, the applicator can be used with any type and any size applicator.

The tampon applicator 20 shown in FIGS. 1–3 is by way of illustration only. The applicator 20 has a discrete plunger 28 and a discrete barrel 22 with a petal tipped tampon ejection end 13 and an opposite or plunger receiving end 24 which, preferably, has fingergrips 25 on the exterior surface thereof. The tampon ejection end 23 is positioned in the closed end of the main portion 12 so that the plunger receiving end 24 is positioned towards and extends into the top portion 14 of the wrap 10.

The score line 16 can be placed in any predetermined location on the wrap 10 with the exact criteria for determining the actual location varying depending on the type of applicator used in conjunction with the wrap 10. Nevertheless, the wrap, for all type applicators, should separate so as to provide for easy grasping and removal of the plunger from the wrap.

When the wrap 10 is used with a conventional length tampon applicator, the wrap, upon separation, should expose a sufficient amount of the free end of the plunger to provide for easy grasping of the plunger such that the assembled tampon applicator can readily be removed from the wrap.

For a compact tampon applicator, such as, for example, the tampon applicator 20 shown in FIGS. 1-3, the score line 16 is positioned at a predetermined location on the wrap so that upon separation of the main portion 12 from the top portion 14, as shown in FIGS. 2 and 3, the fingergrips 25 of the barrel 22 and one end 29 of the plunger 28 are exposed. Specifically, the score line 16 is positioned on the wrap 10 so that upon separation of the wrap a sufficient amount of the plunger is exposed to provide for easy grasping and removal of the plunger 28 from the wrap. Further, the score line 16 should also be positioned so that upon separation of the wrap 10 all or part of the fingergrips 25 of the barrel 22 are exposed to enable the user to readily align the plunger 28 with the barrel and, if desired, permit the user to grasp the fingergrips of the barrel to remove the assembled tampon applicator from the wrap 10. Therefore, the score line 16 should be positioned to expose an end of the plunger and the barrel 22 anywhere along the fingergrips 25, i.e. anywhere from where the fingergrips meet the remainder of the barrel 22 up to the edge of the plunger receiving end 24 of the barrel. In the embodiment shown in FIGS. 1-3, the score line 16 is positioned approximately in the same vertical plane where the fingergrips 25 meet the remainder of the barrel 22 of the tampon applicator 20 so that the user of the tampon applicator 20 can grasp the barrel anywhere along the entire axial extent of the fingergrips 25.

In practice, the score line 16 shown in FIGS. 1-3 is placed at the predetermined location which normally is measured from one of the end seals 17, 18 of the wrap 10 an amount approximately equal to the length of the barrel of the applicator. For example, the barrel 22 of the applicator must be placed in the wrap 10 with sufficient axial space 30 in the wrap 10 between the end seals 17, 18 and the barrel 22 so that the barrel does not apply stress on the end seals. Nevertheless, it has been found that the axial extent of the non-fingergrip portion of the barrel 22 defines the approximate distance of the score line 16 from the end seal 17 of the body portion 12. Thus, for the two piece applicator shown in the figures, which has a non-fingergrip barrel portion of approximately two and one quarter inches, the distance of the score line 16 from the end seal 17 is approximately two and one quarter inches. (The distance of the score line 16 from the end seal 18 of the top portion 14 is approximately 1.65 inches +/−0.12 inches).

To open the wrap 10, the user simply grasps the main portion 12 and the top portion 14 of the wrap 10 and pulls the wrap axially outward using approximately 4 to 9 lbs. of pressure. It is recommended that the user hold the main portion 12 of the wrap 10 between the thumb and the index finger of one hand and grasp, with the other hand, the top portion 14 of the wrap approximately at the end seal of the top portion. The user then snaps off the top portion 14 from the main portion 12. Once the main portion 12 has been separated from the top portion 14, the user can grasp the applicator at the predetermined location.

In the case of a two piece portable tampon applicator, such as the side by side tampon applicator shown in FIGS. 1-3, which applicator requires assembly prior to use, the user grasps the exposed end 29 of the plunger 28, removes the plunger from the wrap and inserts the opposite end of the plunger into the plunger receiving end 24 of the barrel 22 while the barrel is held by the user in the main portion 12 of the wrap 10.

For use with all sized applicators, the main portion 12 of the wrap 10 retains its integrity after separation from the top portion 14 of the wrap. The used tampon applicator can, therefore, be re-inserted into the main portion 12 of the wrap 10. Thus, the main portion 12 of the wrap provides a structure for discreet discarding of the used tampon applicator.

For a conventional length applicator, the main portion 12 of the wrap 10 may include closure means (not shown). Specifically, the closure means is adapted to close the open end, or score line end, of the main portion 12 of the wrap 10 after the used tampon applicator is inserted therein.

For all tampon applicators used with the wrap 10 of the present invention, the score line 16 is positioned on the wrap so that when the wrap opens only the desired portion of the applicator is exposed. Therefore, it can be virtually assured that the user will not contaminate the tampon ejection end 23 of the tampon applicator 20 since the wrap can prevent the user from soiling or contacting the tampon ejection end of the barrel 22.

While the above wrap has been illustrated in connection with a two piece applicator in which the barrel houses the tampon, it can also be used with a two piece applicator in which the plunger component houses the tampon. Further, the wrap may even be used with a retractable one-piece applicator or a hinged or any other compact applicator. Moreover, the wrap can readily be used with a conventional length applicator.

Having thus described the invention with particular reference to the preferred forms thereof, it will be obvious that various changes and modifications may be made therein without departing from the spirit and scope of the invention as defined by the appended claims.

Wherefore, we claim:

1. A tampon package assembly comprising: a tampon applicator having a barrrel member for containing a tampon therein and a plunger member for reciprocal movement within said barrel member to eject the tampon from said barrel member, said barrel member having a fingergrip region at one end and a tampon ejection end at its opposite end; and a protective wrap having a hollow body for initially containing said tampon applicator therein and having a single score line located at a predetermined position along said wrap to separate said wrap into first and second discrete portions; and said barrel and plunger members initially sealed in said protective wrap in adjacent side-by-side relationship; and said second wrap portion including opposed first and second ends, said first end located at said score line and means sealing said second end; and said score line extending transverse to the sealed applicator members contained therein, overlying the barrel member at its fingergrip region and an end region of the plunger, said score line spaced from the end termini of said barrel fingergrip region and plunger end region in the direction of said second end of the second wrap portion; and said tampon applicator members remaining in said second portion of the opened wrap with said barrel fingergrip region and plunger end region extending outwardly of the first end of said second wrap portion for grasping by a user for ready removal of said plunger from the wrap while said barrel member remains within said second wrap portion with its tampon ejection end located at, and completely protectively enclosed by, said sealed first end of the second wrap portion, whereby the barrel member may be manually grasped from about said second wrap portion while said plunger member is manually removed therefrom and inserted in said barrel member.

2. The tampon assembly of claim 1, wherein said score line is a single straight line.

3. The tampon assembly of claim 2, wherein said score line extends circumferentially about said wrap.

4. The tampon assembly of claim 1, wherein said score line is strong enough to withstand approximately 4 to 9 lbs. of pressure.

5. The tampon assembly of claim 1, further including an end seal at each end of said wrap, wherein said score line and each end seal are in different planes, and wherein the plane which contains said score line is substantially parallel to the planes which contain the end seals.

6. The tampon applicator assembly of claim 1, wherein one of said wrap portions is adapted to retain its integrity after separation and tampon applicator removal said wrap portion providing disposal means for subsequent placement of said tampon applicator therein after the tampon has been ejected.

7. The method of packaging and assembly a tampon comprising the steps of:

placing a tampon barrel having opposed tampon insertion and fingergrip ends and a plunger in side-by-side longitudinal relationship within an enclosed wrap, providing a transverse score line along an intermediate portion of the wrap enveloping the enclosed barrel and plunger, opening and removing a portion of the wrap at the score line while retaining the major portions of the barrel and plunger, including the insertion end of the barrel, within a closed portion of the remaining wrap, while the fingergrip end of the barrel and an end of the plunger extend out of the remaining wrap portion, grasping the outwardly extending end of the plunger and removing the plunger from the remaining portion of the wrap while protectively holding the insertion end of the barrel within the closed portion of the remaining wrap, inserting the plunger within the fingergrip end of the barrel while the barrel is manually held within the remaining portion of the opened wrap with its insertion end covered by the closed portion of the wrap and, completely removing the assembled barrel and plunger from the wrap.

8. The method of claim 7, further including the steps of:

reciprocating the plunger within the barrel to eject the tampon from the barrel, and replacing the empty applicator within a portion of the wrap for discarding the applicator after use.

* * * * *